United States Patent
Lee et al.

(10) Patent No.: US 11,661,616 B2
(45) Date of Patent: *May 30, 2023

(54) MICROORGANISM HAVING INCREASED GLYCINE PRODUCTIVITY AND METHOD FOR PRODUCING FERMENTED COMPOSITION USING THE SAME

(71) Applicant: CJ CHEILJEDANG CORPORATION, Seoul (KR)

(72) Inventors: Ji Yeon Lee, Seoul (KR); Jin Sook Chang, Seoul (KR); Hyung Joon Kim, Seoul (KR); Byoung Hoon Yoon, Seoul (KR); Sun Hyoung Choi, Seoul (KR); Yunjung Choi, Seoul (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 225 days.

This patent is subject to a terminal disclaimer.

(21) Appl. No.: 16/638,974

(22) PCT Filed: Mar. 27, 2019

(86) PCT No.: PCT/KR2019/003568
§ 371 (c)(1),
(2) Date: Feb. 13, 2020

(87) PCT Pub. No.: WO2019/190193
PCT Pub. Date: Oct. 3, 2019

(65) Prior Publication Data
US 2021/0002655 A1 Jan. 7, 2021

(30) Foreign Application Priority Data
Mar. 27, 2018 (KR) .......................... 10-2018-0035156

(51) Int. Cl.
| | | |
|---|---|---|
| *C12N 9/10* | (2006.01) | |
| *C12P 13/04* | (2006.01) | |
| *C12N 9/14* | (2006.01) | |
| *C12P 13/14* | (2006.01) | |
| *C12N 15/77* | (2006.01) | |
| *C12N 1/20* | (2006.01) | |

(52) U.S. Cl.
CPC ................ *C12P 13/04* (2013.01); *C12N 1/20* (2013.01); *C12N 9/1077* (2013.01); *C12N 9/14* (2013.01); *C12N 15/77* (2013.01); *C12P 13/14* (2013.01); *C12Y 204/02017* (2013.01); *C12Y 306/01031* (2013.01); *C12N 2830/55* (2013.01)

(58) Field of Classification Search
None
See application file for complete search history.

(56) References Cited

FOREIGN PATENT DOCUMENTS

| KR | 10-2013-0130377 | 12/2013 |
|---|---|---|
| KR | 10-2015-0143699 | 12/2015 |
| KR | 10-2016-0072278 | 6/2016 |
| WO | 2019/027267 A2 | 2/2019 |

OTHER PUBLICATIONS

Namroud et al., South African Journal of Animal Science 40(3): 238-244 (2010).*
Zhang et al., Biochimie 94: 829-838 (2012).*
Schendzielorz et al., "Taking Control over Control: Use of Product Sensing in Single Cells to Remove Flux Control at Key Enzymes in Biosynthesis Pathways," *ACS Synth. Biol.* 3:21-29 (2014).
GenBank: CP025534.1, Corynebacterium glutamicum strain HA chromosome, complete genome, (665 pages) Dec. 27, 2017.
Kjeldsen, "Optimization of an industrial L-lysine producing Corynebacterium glutamicum strain," *DTU Library*, downloaded from orbit.dtu.dk on: Jun. 18, 2019 (188 pages).
Kulis-Horn et al., "Histidine biosynthesis, its regulation and biotechnological application in Corynebacterium glutamicum," *Microbial Biotechnology* 7(1):5-25 (2014).
Kulis-Horn et al., "*Corynebacterium glutamicum* ATP-phosphoribosyl transferases suitable for $_L$-histidine production—Strategies for the elimination of feedback inhibition," *Journal of Biotechnology* 206:26-31 (2015).
NCBI Reference Sequence: WP_003856149.1, "Multispecies: ATP phosphoribosyltransferase [*Corynebacterium*]," (1 page) (Aug. 29, 2013).
Schwentner et al., "Modular systems metabolic engineering enables balancing of relevant pathways for $_L$-histidine production with *Corynebacterium glutamicium*," *Biotechnol Biofuels* 12:65 (21 pages) (2019).

* cited by examiner

Primary Examiner — Erin M. Bowers
(74) Attorney, Agent, or Firm — Seed IP Law Group LLP

(57) ABSTRACT

The present disclosure relates to a microorganism having increased glycine productivity and a method for producing a fermented composition using the microorganism, and more specifically, to a microorganism of the genus *Corynebacterium* having increased glycine productivity due to the introduction of a mutation in HisG, a method for preparing a fermented composition comprising glycine and glutamic acid using the microorganism of the genus *Corynebacterium*, and the fermented composition.

7 Claims, No Drawings
Specification includes a Sequence Listing.

MICROORGANISM HAVING INCREASED GLYCINE PRODUCTIVITY AND METHOD FOR PRODUCING FERMENTED COMPOSITION USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_464USPC_SEQUENCE_LISTING.txt. The text file is 10 KB, was created on Feb. 10, 2020, and is being submitted electronically via EFS-Web.

TECHNICAL FIELD

The present disclosure relates to a microorganism having increased glycine productivity and a method for producing a fermented composition using the microorganism, and more specifically, to a microorganism of the genus *Corynebacterium* having increased glycine productivity due to the introduction of a mutation in HisG, a method for preparing a fermented composition comprising glycine and glutamic acid using the microorganism of the genus *Corynebacterium*, and the fermented composition.

BACKGROUND ART

L-Amino acids are the basic building blocks of proteins and are used as important materials such as pharmaceutical raw materials, food additives, animal feeds, nutritional supplements, pesticides, bactericides, etc. Among these, L-glutamic acid is a representative amino acid produced by fermentation and has a unique, distinctive taste (umami taste), and thus is an important amino acid widely used in the food field as well as in the medical field and other animal feed fields. Further, glycine is mainly used as a flavor enhancer in the food industry because of its sweet taste, and is used with natural flavor enhancers to enhance taste. Furthermore, glycine is also used for its antioxidant activity, buffering action, etc., and in terms of medicine, it is used in infusion solutions, antacids, multi-amino acid preparations, and nutritional supplements.

A typical method for producing amino acids includes a fermentation method using a microorganism of the genus *Brevibacterium* or *Corynebacterium* (Amino Acid Fermentation, Gakkai Shuppan Center: 195-215, 1986) or using *Escherichia coli* or microorganisms of the genera *Bacillus, Streptomyces, Penicillum, Klebsiella, Envinia, Pantoea*, etc. (U.S. Pat. Nos. 3,220,929 and 6,682,912). In addition, such amino acids are also produced by an industrial method using a synthetic process such as the monochloroacetic acid method, the Strecker method, etc.

Additionally, various studies have been conducted for efficiently producing amino acids; for example, efforts have been made to develop microorganisms or fermentation process technologies for producing amino acids with high efficiency. Particularly, specific approaches to target materials have been developed, such as enhancement of expression of genes encoding enzymes involved in the biosynthesis of the amino acids in the strain of the genus *Corynebacterium* or deletion of genes unnecessary for the biosynthesis of amino acids (Korean Patent Nos. 10-0924065 and 1208480). In addition to these methods, a method for removing genes that are not involved in the production of amino acids and a method for removing genes whose functions for producing amino acids are not specifically known have also been utilized. However, there is still a growing need to study methods for efficiently producing amino acids with high yield.

DISCLOSURE

Technical Problem

The present inventors have made efforts to develop a method capable of simultaneously producing several amino acids, and as a result, they have confirmed that when the HisG activity of a microorganism capable of producing glutamic acid is enhanced compared to that of its parent strain, the glycine-producing ability can be improved while maintaining the glutamic acid-producing ability, thereby completing the present disclosure.

Technical Solution

An objective of the present disclosure is to provide a microorganism of the genus *Corynebacterium* having increased glycine productivity, wherein the activity of ATP phosphoribosyltransferase (HisG) is enhanced.

Another objective of the present disclosure is to provide a method for preparing a fermented composition comprising glycine and glutamic acid, comprising fermenting by culturing the microorganism of the genus *Corynebacterium*.

Still another objective of the present disclosure is to provide a fermented composition prepared by the above method.

Advantageous Effects

Since the HisG mutation of the present disclosure can be introduced into a microorganism and produce glutamic acid and glycine simultaneously, it can be effectively used for the production of amino acids. In addition, the present disclosure can improve the taste and palatability of a fermented product by regulating the amounts of glutamic acid and glycine in the fermented product for the preparation of a fermented broth and its application in seasoning products.

BEST MODE

Hereinbelow, the present disclosure will be described in detail. Meanwhile, each description and embodiment disclosed in the present disclosure may be applied to other descriptions and embodiments. That is, all combinations of various elements disclosed in the present disclosure fall within the scope of the present disclosure. Further, the specific descriptions disclosed below should not be construed as limiting the scope of the present disclosure.

To achieve the objectives above, an aspect of the present disclosure provides a microorganism of the genus *Corynebacterium* having increased glycine productivity, wherein the activity of ATP phosphoribosyltransferase (HisG) is enhanced.

Specifically, a microorganism having increased glycine productivity, wherein, in the ATP phosphoribosyltransferase, the $233^{rd}$ amino acid of an amino acid sequence of SEQ ID NO: 4 is substituted with histidine (H), may be provided.

Additionally, specifically, a microorganism having increased glycine productivity, wherein, in the ATP phosphoribosyltransferase, the $233^{rd}$ and $235^{th}$ amino acids of an amino acid sequence of SEQ ID NO: 4 are substituted with histidine (H) and glutamine (Q), respectively, may be provided.

As used herein, the term "ATP phosphoribosyltransferase", which is also called "HisG", refers to an enzyme involved in the histidine synthesis pathway. The histidine synthesis pathway consists of a total of 9 enzymes (HisG-HisE-HisI-HisA-HisH-HisB-HisC-HisN-HisD), and HisG constitutes the first step thereof.

It has been known that the HisG is involved in the production of histidine, but the relationship thereof with the production of glycine is not known and was first identified by the present inventors. More specifically, the present inventors have confirmed for the first time that the amount of glycine production can be increased by enhancing the activity of HisG. In particular, HisG is subject to feedback inhibition by the product histidine, and in the present disclosure, a mutation was introduced in which the histidine feedback inhibition is released, and as a result, the effects of increasing the amount of glycine production and maintaining the amount of glutamic acid were first identified by the present inventors.

As used herein, the term "enhancement of HisG activity" means that the activity of HisG enzyme is increased compared to the endogenous activity possessed by a microorganism of the genus Corynebacterium in its natural state. Examples of the methods of increasing the HisG activity may include: (i) a method of increasing the copy number of a nucleotide sequence encoding the enzyme by a method of further inserting a polynucleotide containing a nucleotide sequence encoding HisG into the chromosome, or by a method of introducing a polynucleotide containing a nucleotide sequence encoding HisG into a vector system, etc.; (ii) a method of enhancing the promoter of the hisG gene (e.g., replacement with a stronger promoter, introduction of a mutation on the promoter, etc.); (iii) a method of modifying the enzyme with stronger activity by gene mutation, etc.

Specifically, in the present disclosure, the $233^{rd}$ amino acid of the HisG amino acid sequence of SEQ ID NO: 4 (i.e., glycine) may be substituted with histidine; or in the HisG amino acid sequence of SEQ ID NO: 4, the $233^{rd}$ amino acid (i.e., glycine) may be substituted with histidine and the $235^{th}$ amino acid (i.e., threonine) may be substituted with glutamine. Accordingly, the microorganism of the genus Corynebacterium comprising modified HisG as described above can significantly increase glycine productivity while maintaining the glutamic acid productivity without any adverse effect thereon. The increase in glycine productivity may mean that the glycine productivity is increased compared to a microorganism having HisG without the modification of the present disclosure (i.e., HisG without the above mutation).

In another embodiment, the promoter of HisG enzyme may be modified via mutation or substitution to a promoter stronger than the native promoter. An improved promoter or heterogeneous promoter with a nucleotide substitution mutation may be linked instead of the endogenous enzyme promoter, and examples of the heterogeneous promoter may include cj7 promoter, lysCP1 promoter, EF-Tu promoter, groEL promoter, aceA promoter, aceB promoter, etc., but the heterogeneous promoter is not limited thereto.

Additionally, since the hisG gene consists of a hisE gene and an operon, the activity of HisG enzyme can be enhanced by overexpression of hisG via mutation or substitution of the promoter sequence of the hisEG gene. More specifically, the activity of HisG enzyme can be enhanced using a promoter stronger than the native promoter prepared by a mutation in the promoter sequence of the hisEG gene, in which in the nucleotide sequence of SEQ ID NO: 1, the $53^{rd}$ and $55^{th}$ nucleotides are substituted with T; or the $53^{rd}$ and $55^{th}$ nucleotides are substituted with T and the $60^{th}$ nucleotide is substituted with G. Reviewing the literature on the studies of promoter sequences of Corynebacterium glutamicum (Microb Biotechnol. 2013 Mar.; 6(2): 103-117), it is possible to detect the positions of multiple transcriptional start points (TSPs) and promoters by RNA sequencing (RNA-seq). As such, the present inventors have confirmed the promoter sequence of the hisEG gene via RNA-seq experiments on the ATCC13869 strain, and additionally, have attempted to induce overexpression of the promoter sequence of the hisEG gene via mutation of its native promoter. As a method for modifying the native promoter, the nucleotide sequences at positions −35 and −10 from the promoter region of Corynebacterium glutamicum may be modified such that the modified promoter sequence becomes close to the consensus sequence. In particular, when the sequence at the −10 region (TATA box) from the promoter sequence of the hisEG gene is modified to be close to the consensus sequence, the promoter may be modified to a promoter which is stronger compared to the native promoter.

Specifically, the ATP phosphoribosyltransferase, which is included in the microorganism of the genus Corynebacterium, may consist of an amino acid sequence of SEQ ID NO: 5 or SEQ ID NO: 6.

Additionally, the amino acid sequences of the present disclosure may be modified by known mutagenesis methods, such as directed evolution, site-directed mutagenesis, etc.

Therefore, the ATP phosphoribosyltransferase may include HisG including a nucleotide sequence that has a homology to the amino acid sequence of SEQ ID NO: 5 or SEQ ID NO: 6 of at least 60%, specifically at least 70%, more specifically at least 80%, and even more specifically at least 83%, at least 84%, at least 88%, at least 90%, at least 93%, at least 95%, or at least 97%. It is apparent that any amino acid sequence having such homology, in which part of the sequence is deleted, modified, substituted, or added, is also within the scope of the present disclosure, as long as the resulting amino acid sequence has a biological activity substantially equivalent or corresponding to the amino acid sequence of SEQ ID NO: 5 or SEQ ID NO: 6.

In particular, the term "L-glutamic acid" or "L-glutamate" refers to a kind of amino acid which is classified as a non-essential amino acid. L-Glutamic acid is known to be the most common excitatory neurotransmitter in the central nervous system. In addition, since L-glutamic acid has an umami taste, monosodium glutamate (MSG) has been developed therefrom and is widely used as a flavor enhancer. It is generally produced through fermentation of microorganisms producing L-glutamic acid.

Additionally, the term "glycine" refers to an amino acid having a colorless crystalline form and a sweet taste. Glycine is mainly used as a flavor enhancer for foods, and in terms of medicine, it is used in infusion solutions, antacids, multi-amino acid preparations, and nutritional supplements. In general, glycine is prepared by an industrial synthetic method such as the monochloroacetic acid method, the Strecker method, etc. However, there is an inconvenience in that since a mixture of D-type and L-type amino acids are produced when amino acid is prepared using the synthetic method, it is necessary to perform optical resolution. Therefore, it is required to prepare glycine by a fermentation method which has various advantages, i.e., the reaction conditions are moderate, mass production is possible in a short period of time, the process is environmentally friendly, and the material produced is biodegradable.

As used herein, the term "homology" may indicate the degree of matching with a given amino acid sequence or nucleotide sequence, and may be presented as a percentage (%). In the present disclosure, a homology sequence having an activity which is identical or similar to the given amino acid sequence or nucleotide sequence is presented as "% homology". The homology to the amino acid sequence or nucleotide sequence can be determined by, for example, the algorithm BLAST (see Karlin and Altschul, *Pro. Natl. Acad. Sci. USA*, 90, 5873 (1993) or FASTA (see Pearson, *Methods Enzymol.*, 183, 63, 1990). Based on this algorithm BLAST, the programs BLASTN and BLASTX have been developed (see http://www.ncbi.nlm.nih.gov).

As used herein, the term "stringent conditions" refers to conditions which permit specific hybridization between polynucleotides. Such stringent conditions are specifically described in the literature (e.g., J. Sambrook et al.). For example, the stringent conditions may include conditions in which genes having a high homology (e.g., 60% or more, specifically 90% or more, more specifically 95% or more, even more specifically 97% or more, and even more specifically 99% or more) can hybridize with each other, whereas genes having a lower homology thereof cannot hybridize with each other; or conditions for conventional Southern hybridization (i.e., conditions for washing once, and specifically two or three times at a salt concentration and temperature corresponding to 60° C., 1×SSC, 0.1% SDS, specifically at 60° C., 0.1×SSC, 0.1% SDS; and more specifically at 68° C., 0.1×SSC, 0.1% SDS). Hybridization requires that two nucleotides have complementary sequences, although mismatches between bases are possible depending on the stringency of hybridization. The term "complementary" is used to describe the relationship between nucleotide bases that can hybridize with each other. For example, with respect to DNA, adenosine is complementary to thymine and cytosine is complementary to guanine. Therefore, the present disclosure may also include substantially similar nucleotide sequences as well as isolated polynucleotide fragments complementary to the entire sequence.

Specifically, the polynucleotide having homology may be detected using hybridization conditions including a hybridization step at a $T_m$ value of 55° C. under the above-described conditions. In addition, the $T_m$ value may be 60° C., 63° C., or 65° C., but is not limited thereto. One of ordinary skill in the art can appropriately adjust the $T_m$ value according to its purpose. The appropriate stringency of hybridizing the polynucleotides is dependent on the length and degree of complementarity of the polynucleotides, and the variables are well known in the art (see Sambrook et al., supra, 9.50-9.51, 11.7-11.8).

As used herein, the term "microorganism" includes all of a wild-type microorganism and a naturally or artificially genetically modified microorganism, and it may be a microorganism having a particular attenuated or reinforced mechanism due to insertion of an exogenous gene or reinforcement or attenuation of activity of an endogenous gene.

In the present disclosure, the microorganism may include the ATP phosphoribosyltransferase. Additionally, the ATP phosphoribosyltransferase may be introduced into the microorganism by transformation via a vector, but the method of transformation is not limited thereto. Furthermore, it does not matter whether the gene encoding the HisG is located on the chromosome or outside of the chromosome as long as the HisG can be expressed in the microorganism.

As used herein, the term "vector" is an artificial DNA molecule having a genetic material capable of expressing a target gene in an appropriate host, and may refer to a DNA construct including a nucleotide sequence of the gene encoding the HisG.

The vector used in the present disclosure is not particularly limited as long as it can be expressed in a host cell, and any vector known in the art may be used to transform the host cell. Examples of the conventional vector may include natural or recombinant plasmids, cosmids, viruses, and bacteriophages.

For example, as a phage vector or cosmid vector, pWE15, M13, λLB3, λBL4, λIXII, λASHII, λAPII, λt10, λt11, Charon4A, Charon21A, etc. may be used; and as a plasmid vector, those based on pBR, pUC, pBluescriptII, pGEM, pTZ, pCL, pET, etc. may be used.

Additionally, a polynucleotide encoding the HisG of the present disclosure may be introduced into the chromosome of a host cell via a vector for chromosomal insertion in the host cell. For example, vectors pECCG117, pDZ, pACYC177, pACYC184, pCL, pUC19, pBR322, pMW118, pCC1BAC, pCES208, pXMJ19, etc. may be used, but the vectors are not limited thereto.

Additionally, the insertion of the polynucleotide into the chromosome may be accomplished by any method known in the art, e.g., by homologous recombination.

Since the vector of the present disclosure can be inserted into the chromosome by inducing homologous recombination, the selection marker may be additionally included to confirm successful insertion of a gene into the chromosome. A selection marker is for screening the cells which are transformed with the vector, in other words, for determining whether the polynucleotide is inserted. The markers that provide selectable phenotypes such as drug resistance, auxotrophy, resistance to toxic agents, or expression of surface proteins may be used. In an environment treated with a selective agent, only the cells expressing the selection marker can survive, or the cells show a different phenotype, and thus the successfully transformed cells can be selected through this method.

As used herein, the term "transformation" refers to the introduction of the vector comprising the polynucleotide or the gene encoding HisG into a host cell in order to allow the expression of the gene and the HisG in the host cell. Furthermore, as long as the target gene can be expressed in the host cell, it does not matter whether the transformed gene is located on the chromosome of the host cell or outside of the chromosome, and both cases are included.

The transformation method may include all methods of introducing the gene into a cell, and may be carried out by selecting a suitable standard technique known in the art depending on the host cell. For example, a suitable standard technique may be selected among electroporation, calcium phosphate ($CaPO_4$) precipitation, calcium chloride ($CaCl_2$) precipitation, microinjection, a polyethyleneglycol (PEG) technique, a DEAE-dextran technique, a cationic liposome technique, and a lithium acetate-DMSO technique, but the suitable standard technique is not limited thereto.

In the present disclosure, the microorganism may be any microorganism without limitation, in which the HisG of the present disclosure is introduced and thus the glycine productivity is increased.

Specifically, the microorganism may be a microorganism of the genus *Corynebacterium;* more specifically *Corynebacterium glutamicum* or *Corynebacterium flavum;* and most specifically *Corynebacterium glutamicum,* but the microorganism is not limited thereto.

Another aspect of the present disclosure provides a method for preparing a fermented composition, comprising fermenting by culturing the microorganism of the genus *Corynebacterium* in a medium.

Still another aspect of the present disclosure provides a fermented composition prepared by the above method.

The fermented composition may be one in which the amount of glycine is increased.

The microorganism is as described above.

As used herein, the term "culture" refers to culturing of a microorganism under artificially controlled environmental conditions. In the present disclosure, the method for producing a target material using a microorganism may be carried out by a method widely known in the art. Specifically, the culture may be carried out in a batch process or in a continuous process (e.g., a fed-batch process or repeated fed-batch process), but the batch process is not limited thereto. The medium used for the culture must satisfy the requirements of a particular strain employed. The culture medium suitable for use in culturing the *Corynebacterium* strain is known in the art (e.g., Manual of Methods for General Bacteriology by the American Society for Bacteriology, Washington D.C., USA, 1981).

Carbon sources that can be used in the culture medium may be saccharides and carbohydrates (e.g., glucose., sucrose, lactose, fructose, maltose, starch, and cellulose); oils and lipids (e.g., soybean oil, sunflower seed oil, peanut oil, and coconut oil); fatty acids (e.g., palmitic acid, steric acid, and linoleic acid); alcohols (e.g., glycerol and ethanol); and organic acids (e.g., acetic acid). These materials may be used independently or in combination, but the modes of use are not limited thereto.

Examples of nitrogen sources that can be used include peptone, yeast extract, meat juice, malt extract, corn steep liquor, soybean meal, and urea, or inorganic compounds (e.g., ammonium sulfate, ammonium chloride, ammonium phosphate, ammonium carbonate, and ammonium nitrate). These nitrogen sources may also be used independently or in combination, but the modes of use are not limited thereto.

Phosphorous sources that can be used in the culture medium may include dipotassium hydrogen phosphate, potassium dihydrogen phosphate, or corresponding sodium-containing salts. In addition, the culture medium may contain metal salts necessary for the growth of cells. Finally, in addition to the materials above, materials essential for growth (e.g., amino acids and vitamins) may be used. Further, precursors suitable for the culture medium may be used. The above raw materials may be adequately fed into the culture in a batch or continuous manner.

During the culture of the microorganism, the pH of the culture may be adjusted by an appropriate basic compound (e.g., sodium hydroxide, potassium hydroxide, or ammonia) or an acidic compound (e.g., phosphoric acid or sulfuric acid). Foaming may be adjusted by an anti-foaming agent (e.g., fatty acid polyglycol ester). The aerobic condition of the culture may be maintained by introducing oxygen or oxygen-containing gas (e.g., air).

The temperature of the culture (medium) may be generally in a range of 20° C. to 45° C., and specifically 25° C. to 40° C. Culturing may be continued until the desired production amount of the target material is obtained, and specifically for 10 to 160 hours.

The recovery of the target material from the culture (medium) may be performed by a conventional separation method known in the art. For the separation method, methods such as centrifugation, filtration, chromatography, crystallization, etc. may be used. For example, a supernatant obtained by centrifugation of the culture medium at a low speed to remove biomass may be separated by ion-exchange chromatography, but the separation method is not limited thereto. In an alternative method, the target material may be recovered by performing processes of separation and filtration of bacterial cells from a culture product (medium) without an additional purification process. In another alternative method, the recovery step may further include a purification process.

As used herein, the term "the fermented composition" refers to a composition obtained by culturing the microorganism of the present disclosure. Furthermore, the fermented composition may include a composition in the form of a liquid or powder obtained after culturing the microorganism followed by a suitable post-treatment. In particular, the suitable post-treatment process may include, for example, a process of culturing the microorganism, a process of removing bacterial cells, a concentration process, a filtration process, and a process of mixing carriers, and may further include a drying process. In some cases, the post-treatment process may not include a purification process. The fermented composition, obtained by culturing the microorganism of the present disclosure, contains an increased amount of glycine while maintaining a certain level of glutamic acid production, thus making it possible to provide an optimum taste.

Additionally, "the fermented composition" does not exclude seasoning products (e.g., powdered soup products, snack seasoning products, etc.) containing a composition in the form of a liquid or powder. Furthermore, "the fermented composition" does not exclude cases in which a material obtained by a non-fermentation process and/or another material obtained by a non-natural process is further included, as long as the composition obtained by culturing the microorganism of the present disclosure is contained therein.

MODE FOR INVENTION

Hereinbelow, the present disclosure will be described in detail with accompanying exemplary embodiments. However, the exemplary embodiments disclosed herein are only for illustrative purposes and should not be construed as limiting the scope of the present disclosure.

EXAMPLE 1

Introduction of Mutation Into KFCC11074 Strain for Increasing Glycine Productivity and Confirmation of Production Amounts of Glutamic Acid and Glycine in KFCC11074 Into Which Mutation is Introduced

EXAMPLE 1-1

Preparation of Vector Where Mutation is Introduced

To confirm the effect of enhancing HisG activity on the increase of glycine productivity in a strain capable of producing glutamic acid, a strain into which a mutation was induced within a promoter of the hisEG gene and a strain into which histidine feedback inhibition release mutation was induced, and the glycine productivity of these strains was examined.

Meanwhile, the genes hisE and hisG are composed of operons, and these genes are involved in the histidine biosynthesis pathway. In particular, since the HisG is feedback-inhibited by the product histidine, attempts were made to confirm whether the glycine productivity of these strains could be increased when the feedback inhibition release mutation is introduced to increase the activity of the hisG gene. As such, attempts were made to introduce each of a hisEG promoter mutation and a feedback inhibition release mutation into the strain KFCC11074 (Korean Patent No. 10-0292299), which is known as a glutamic acid-producing strain. Specifically, a vector for gene substitution was prepared in order to substitute the $53^{rd}$ and $55^{th}$ nucleotides of the polynucleotide sequence of SEQ ID NO: 1, which includes the hisEG promoter, with T; and to substitute the $53^{rd}$ and $55^{th}$ nucleotides of the polynucleotide sequence of SEQ ID NO: 1 with T and the $60^{th}$ nucleotide of the polynucleotide sequence of SEQ ID NO: 1 with G.

Additionally, vectors for gene substitution were prepared in order to substitute the $233^{rd}$ amino acid (i.e., glycine (Gly/G)) of the amino acid sequence of HisG of SEQ ID NO: 4 with histidine (His/H), and to substitute the $233^{rd}$ amino acid (i.e., glycine (Gly/G)) and $235^{th}$ amino acid (i.e., threonine (Thr/T)) of the amino acid sequence of HisG of SEQ ID NO: 4 with histidine (His/H) and glutamine (Gln/Q), respectively. Gene fragments for the preparation of each substitution vector were obtained by PCR using the ATCC13869 genomic DNA as a template. Each primer pair was prepared based on information on genes and adjacent nucleotide sequences of the *Corynebacterium glutamicum* (ATCC13869) registered in the National Institutes of Health GenBank (NIH GenBank).

To prepare vectors for hisEG promoter substitution, PCR was performed in the following order: (1) denaturation at 95° C. for 5 minutes; (2) a total of 30 cycles of denaturation at 95° C. for 30 seconds, annealing at 55° C. for 30 seconds, and polymerization at 72° C. for 1 minute; and (3) polymerization at 72° C. for 5 minutes. More specifically, the polynucleotide (500 bp) amplified using the primers of SEQ ID NOS: 7 and 8 and the polynucleotide (500 bp) amplified using the primers of SEQ ID NOS: 9 and 10 were obtained. The obtained two DNA fragments were ligated to the vector pDZ (Korean Patent No. 10-0924065 and International Patent Publication No. WO 2008-033001), which had been digested with restriction enzyme SalI, using an infusion enzyme, and thereby a single vector for substitution of two genes, which include hisEG promoter, was prepared, and the vector was named as "pDZ-hisEG-pro-2mt". Additionally, a 500 bp polynucleotide amplified using the primers of SEQ ID NOS: 7 and 11 and a 500 bp polynucleotide amplified using the primers of SEQ ID NOS: 10 and 12 were obtained. The obtained two DNA fragments were ligated to the vector pDZ (Korean Patent No. 10-0924065 and International Publication No. WO 2008-033001), which had been digested with restriction enzyme SalI, using an infusion enzyme, and thereby a single vector for substitution of one gene, which includes hisEG promoter, was prepared, and the vector was named as "pDZ-hisE-pro-3mt". The information on the primer sequences used for the vector preparation is shown in Table 1 below.

To substitute the $233^{rd}$ amino acid with H and substitute the $233^{rd}$ and the $235^{th}$ amino acids with H and Q, respectively, vectors for gene substitution were prepared. Specifically, PCR was performed in the following order: (1) denaturation at 95° C. for 5 minutes; (2) a total of 30 cycles of denaturation at 95° C. for 30 seconds, annealing at 55° C. for 30 seconds, and polymerization at 72° C. for 1 minute; and (3) polymerization at 72° C. for 5 minutes. Additionally, a 722 bp polynucleotide amplified using the primers of SEQ ID NOS: 13 and 14 and a 798 bp polynucleotide amplified using the primers of SEQ ID NOS: 15 and 16 were obtained. The obtained two DNA fragments were ligated to the vector pDZ (Korean Patent No. 10-0924065 and International Publication No. WO 2008-033001), which had been digested with restriction enzyme SalI, using an infusion enzyme, and thereby a single 1.5 kbp vector for gene substitution, which includes a polynucleotide including a HisG(G233H) mutation, was prepared, and the vector was named as "pDZ-hisG(G233H)". Additionally, a 722 bp polynucleotide amplified using the primers of SEQ ID NOS: 13 and 17 and a 798 bp polynucleotide amplified using the primers of SEQ ID NOS: 16 and 18 were obtained. The obtained two DNA fragments were ligated to the vector pDZ (Korean Patent No. 10-0924065 and International Publication No. WO 2008-033001), which had been digested with restriction enzyme SalI, using an infusion enzyme, and thereby a single 1.5 kbp vector for gene substitution, which includes a polynucleotide including a HisG(G233H/T235Q) mutation, was prepared, and the vector was named as "pDZ-hisG(G233H/T235Q)". The information on the primer sequences used for the vector preparation is shown in Table 1 below.

TABLE 1

| SEQ ID NO | Primer | Sequence (5' to 3') |
|---|---|---|
| 7 | hisEG-pro-2mt-AF | GATCCTCTAGAGTCGAC TTCGACGAATCCCTCG |
| 8 | hisEG-pro-2mt-AR | CGGTACATTATACCAC ACAACAGTTATCAATG |
| 9 | hisEG-pro-2mt-BF | GTGGTATAATGTACCG AGTGAAGACATTTGAC |
| 10 | hisEG-pro-2mt-BR | ATGCCTGCAGGTCGAC TGATACCCAAATCGAG |
| 11 | hisEG-pro-3mt-AR | CGGTCCATTATACCAC ACAACAGTTATCAATG |
| 12 | hisEG-pro-3mt-BF | GTGGTATAATGGACCG AGTGAAGACATTTGAC |
| 13 | hisG(G233H)-AF | GATCCTCTAGAGTCGAC CCAAACAAGGGCTCGC |
| 14 | hisG(G233H)-AR | CGTGCCAGTGGGGA TACCGTTGGGTGGG |
| 15 | hisG(G233H)-BF | AACCCCAGGCCTATC CCACCCAACGGTATC |
| 16 | hisG(G233H)-BR | ATGCCTGCAGGTCGACG CAAGGTTGGCAACAAC |
| 17 | hisG(G233H/T235Q)-AR | CGTGCCAGTGGGGAT ACCTGTGGGTGGG |
| 18 | hisG(G233H/T235Q)-BF | AACCCCAGGCCTATC CCACCCACAGGTATC |

EXAMPLE 1-2

Preparation of KFCC11074 Into Which Mutation is Introduced and Confirmation of Production Amounts of Glutamic Acid and Glycine The vectors for hisEG promoter substitution (i.e., pDZ-hisEG-pro-2mt and pDZ-hisEG-pro-3mt) and the vectors for gene substitution (i.e., pDZ-hisG(G233H) and pDZ-hisG (G233H/T235Q)), which had been prepared in Example 1-1, were each introduced into the KFCC11074 strain by electroporation to prepare "KFCC11074_Pro(2mt)_hisEG", "KFCC11074_Pro(3mt)_hisEG", "KFCC11074_hisG (G233H)", and "KFCC11074_hisG(G233H/T235Q)", which are the glutamic acid- and glycine-producing strains into which the mutation was introduced, respectively.

Specifically, these strains were prepared by transformation (*Appl. Microbiol. Biotechnol.*, 1999, 52: 541-545). The strains into which the vectors were inserted on the chromosome by recombination of homologous sequences were selected on an agar nutrient medium containing kanamycin (25 mg/L). The selected primary strains were subjected to a secondary crossover, and each of the strains into which the two or three target mutations were introduced were selected. The mutation (substitution) of the finally transformed strains was confirmed by sequencing after performing PCR using each of the primer pair of SEQ ID NOS: 7 and 10 and the primer pair of SEQ ID NOS: 13 and 16.

Then, the selected strains KFCC11074_Pro(2mt)_hisEG, KFCC11074_Pro(3mt)_hisEG, KFCC11074_hisG(G233H), and KFCC11074_hisG(G233H/T235Q) were plated on a nutrient medium and cultured at 30° C. for 16 hours. A fermentation medium (25 mL), which had been autoclaved at 121° C. for 15 minutes, was dispensed into each Erlenmeyer flask (250 mL) for shaking, and each strain cultured in the nutrient medium was inoculated thereto and cultured for 48 hours. The culture conditions were set to 200 rpm, 37° C., and pH 8.0. The compositions of the nutrient medium and fermentation medium are as follows.

Nutrient Medium:

Glucose 1%, meat juice 0.5%, polypeptone 1%, sodium chloride 0.25%, yeast extract 0.5%, agar 2%, urea 0.2%, pH 7.2

Fermentation Medium:

Raw sugar 6%, calcium carbonate 5%, ammonium sulfate 2.25%, potassium monophosphate 0.1%, magnesium sulfate 0.04%, iron sulfate (10 mg/L), biotin (0.3 mg/L), thiamine hydrochloride (0.2 mg/L)

After completion of the culture, the production amounts of L-glutamic acid and glycine were measured by a method using HPLC, and the measurement results are shown in Table 2 below.

TABLE 2

| Strain | L-Glutamic acid (g/L) | Glycine (mg/L) |
| --- | --- | --- |
| KFCC11074 | 11.5 | 165 |
| KFCC11074_Pro(2mt)_hisEG | 11.4 | 198 |
| KFCC11074_Pro(3mt)_hisEG | 12.0 | 209 |
| KFCC11074_hisG(G233H) | 11.8 | 210 |
| KFCC11074_hisG(G233H/T235Q) | 12.3 | 433 |

As shown in Table 2, it was confirmed that the concentration of L-glutamic acid produced by each of the *Corynebacterium glutamicum* strains KFCC11074_Pro(2mt)_hisEG, KFCC11074_Pro(3mt)_hisEG, KFCC11074_hisG (G233H), and KFCC11074_hisG(G233H/T235Q), into which the mutation was introduced, was similar to that produced by the *Corynebacterium glutamicum* strain KFCC11074 without the mutation.

On the other hand, it was confirmed that the concentration of glycine produced by each of the strains KFCC11074_Pro (2mt)_hisEG, KFCC11074_Pro(3mt)_hisEG, KFCC11074_hisG(G233H), and KFCC11074_hisG (G233H/T235Q) was increased by 33 mg/L, 44 mg/L, and 45 mg/L relative to that produced by the strain KFCC11074, respectively. In particular, the KFCC11074_hisG(G233H/T235Q) strain showed a glycine concentration of 268 mg/L, which is a significant increase.

That is, it was confirmed that the mutations, in which the hisEG promoter mutation and the HisG feedback inhibition release mutation are included, significantly increased the glycine productivity while maintaining the L-glutamic acid productivity in the microorganisms with no significant effect thereon.

EXAMPLE 2

Confirmation of Production Amounts of Glutamic Acid and Glycine in ATCC13869 Into Which Mutation is Introduced To confirm whether the above mutations have an effect of increasing glycine productivity even in wild-type *Corynebacterium glutamicum* ATCC13869 strain without affecting glutamic acid productivity, an attempt was made to prepare a strain based on ATCC13869 into which a mutation is introduced.

The vectors for hisEG promoter substitution (i.e., pDZ-hisEG-pro-2mt and pDZ-hisEG-pro-3mt) and the vectors for gene substitution (i.e., pDZ-hisG(G233H) and pDZ-hisG (G233H/T235Q)), which had been prepared in Example 1-1, were each introduced into the ATCC13869 strain by electroporation to prepare "ATCC13869_Pro(2mt)_hisEG", "ATCC13869_Pro(3mt)_hisEG", "ATCC13869_hisG (G233H)", and "ATCC13869_hisG(G233H/T235Q)", which are the glutamic acid- and glycine-producing strains into which the mutation was introduced, respectively.

Specifically, these strains were prepared by transformation (*Appl. Microbiol. Biotechnol.*, 1999, 52: 541-545). The strains into which the vectors were inserted on the chromosome by recombination of homologous sequences were selected on an agar nutrient medium containing kanamycin (25 mg/L). The selected primary strains were subjected to a secondary crossover, and each of the strains into which the two or three target mutations were introduced were selected. The mutation (substitution) of the finally transformed strains was confirmed by sequencing after performing PCR using each of the primer pair of SEQ ID NOS: 7 and 10 and the primer pair of SEQ ID NOS: 13 and 16.

Each colony was subcultured in a nutrient medium and then cultured in a fermentation medium for 5 hours. Then, 25% Tween 40 was added to each medium at a concentration of 0.4%, and each colony was cultured again for 32 hours.

Nutrient Medium:

Glucose 1%, meat juice 0.5%, polypeptone 1%, sodium chloride 0.25%, yeast extract 0.5%, agar 2%, urea 0.2%, pH 7.2

Fermentation Medium:

Raw sugar 6%, calcium carbonate 5%, ammonium sulfate 2.25%, potassium monophosphate 0.1%, magnesium sulfate 0.04%, iron sulfate (10 mg/L), biotin (0.3 mg/L), thiamine hydrochloride (0.2 mg/L)

Each colony was cultured under the above conditions and the L-glutamic acid concentration was measured using YSI, and the glycine concentration was measured using HPLC. The measured concentrations of L-glutamic acid and glycine are shown in Table 3 below.

TABLE 3

| Strain | L-Glutamic acid (g/L) | Glycine (mg/L) |
|---|---|---|
| ATCC13869 | 13.8 | 117 |
| ATCC13869_Pro(2mt)_hisEG | 13.7 | 128 |
| ATCC13869_Pro(3mt)_hisEG | 14.0 | 135 |
| ATCC13869_hisG(G233H) | 13.5 | 144 |
| ATCC13869_hisG(G233H/T235Q) | 13.7 | 306 |

As shown in Table 3, it was confirmed that the concentration of L-glutamic acid produced by each of the *Corynebacterium glutamicum* strains ATCC13869_Pro(2mt)_hisEG, ATCC13869_Pro(3mt)_hisEG, ATCC13869_hisG (G233H), and ATCC13869_hisG(G233H/T235Q), into which the mutation was introduced, was similar to that produced by the *Corynebacterium glutamicum* strain ATCC13869; however, all of the *Corynebacterium glutamicum* strains ATCC13869_Pro(2mt)_hisEG, ATCC13869_Pro(3mt)_hisEG, ATCC13869_hisG(G233H), and ATCC13869_hisG(G233H/T235Q) showed an increase in glycine concentration compared to the *Corynebacterium glutamicum* strain ATCC13869.

That is, it was reconfirmed that the mutations, in which the hisEG promoter mutation and the HisG feedback inhibition release mutation are included, significantly increased the glycine productivity while maintaining the L-glutamic acid productivity in the microorganisms with no significant effect thereon.

Meanwhile, the strains ATCC13869_hisG(G233H) and ATCC13869_hisG(G233H/T235Q) were deposited at the Korean Culture Center of Microorganisms (KCCM), which is an international depositary authority under the Budapest Treaty, on Mar. 14, 2019, under the strain names of "CA02-9216" and "CA02-9217", and were assigned Accession Nos. "KCCM12458P" and "KCCM12459P".

EXAMPLE 3

Preparation of Fermented Composition for Preparation of Seasoning Products

As described above, it was confirmed that the strains in which the HisG activity was enhanced showed an increase in glycine productivity while showing no significant effect on L-glutamic acid productivity. Therefore, an attempt was made to prepare a fermented composition using a microorganism of the genus *Corynebacterium* of the present disclosure in which the HisG activity was enhanced.

For example, preparation was attempted of a fermented composition using glutamic acid, which is a basic, well-known seasoning material, as an active ingredient, and the fermentation strain and fermentation processes were controlled to increase the proportions of other by-product ingredients of the seasoning materials for the purpose of increasing the constitution of the rich taste.

An attempt was made to prepare a fermented composition in a 5 L fermenter using strains in which both the hisEG promoter mutation and the HisG feedback inhibition release mutation are included.

All of the ingredients used in the preparation of the culture media used were those corresponding to the food grade.

Primary seed medium was prepared as follows:

Glucose (1%), Yeast Extract (1%), Peptone (1%), Ammonium Sulfate (0.1%), NaCl (0.25%), $KH_2PO_4$ (0.15%), $K_2HPO_4$ (0.15%), pH 8.0

Secondary seed medium was prepared as follows:

Organic Raw Sugar (4.6% with a purity of 98.5%), Magnesium Sulfate (0.05%), Yeast Extract (0.5%), $KH_2PO_4$ (0.2%), Iron Sulfate (0.002%), Biotin (1 mg/L), Thiamine HCl (2 mg/L), a small amount of an anti-foaming agent, pH 7.2

Fermentation medium was prepared as follows:

Organic Raw Sugar (4% with a purity of 98.5%), Magnesium Sulfate (0.03%), Yeast Extract (1%), Phosphoric Acid (0.22%), KOH (0.4%), Biotin (0.2 mg/L), Thiamine HCl (0.6 mg/L), Manganese Sulfate (0.002%), Iron Sulfate (0.002%), Zinc Sulfate (0.002%), Copper Sulfate (0.006%), a small amount of an anti-foaming agent, pH 7.4

The primary seed medium (50 mL) was dispensed into each 500 mL shaking Erlenmeyer flask, autoclaved at 121° C. under pressure for 20 minutes. Then, each strain was inoculated and incubated with shaking at a rotation speed of 200 rpm, at 30° C. for 5 to 7 hours.

The secondary seed medium was prepared in an amount of 0.25 L in a 1.5 L test fermenter, autoclaved at 121° C. under pressure for 20 minutes, and cooled. Then, the primary seed medium (50 mL) was inoculated and incubated at a rotation speed of 900 rpm at 31.5° C. for 15 hours.

The fermentation medium was prepared in an amount of 0.25 L in a 5 L test fermenter, autoclaved at 121° C. under pressure for 20 minutes, and cooled. Then, the secondary seed medium (0.26 L) was inoculated thereto and incubated at a rotation speed of 900 rpm at 30° C. to 34° C.

While culturing under the above conditions, the pH of the fermentation culture was continuously adjusted using 28% ammonia water to be in the range of 7.0 to 7.4 during the culture of the *Corynebacterium glutamicum*. When the concentration of the residual sugar in the culture became in the range of 0.5% to 1.5%, sterilized organic raw sugar was frequently added to continue the culture until the total amount of the sugar added became 30% to 34% of the amount of the fermented broth.

TABLE 4

| | Results of Analysis (g/L) | | | | | | |
|---|---|---|---|---|---|---|---|
| | Active Ingredient | | | By-product | | | |
| Strain | Solid | Glutamic Acid | Glycine | Amino Acid | Organic Acid | Residual Sugar | Ions |
| KFCC11074 | 140.2 | 64.2 | 0.18 | 11.5 | 3.5 | 12.0 | 11.1 |
| KFCC11074_hisG(G233H/T235Q)_Pro(3mt)_hisEG | 147.3 | 59.0 | 2.43 | 16.4 | 2.7 | 15.1 | 10.7 |

As a result, as shown in Table 4 above, it was confirmed that although there was no significant difference in the amount of glutamic acid production between the two strains, the amount of glycine in the fermented broth produced by the *Corynebacterium glutamicum* KFCC11074_hisG (G233H/T235Q)_Pro(3mt)_hisEG strain, in which the mutation was introduced, was significantly increased.

Even in a case where a fermented composition was prepared using a 3 kL fermenter, there was no significant difference in the amount of glutamic acid production between the two strains. However, the *Corynebacterium glutamicum* KFCC11074_hisG(G233H/T235Q)_Pro(3mt)_hisEG strain, in which the mutation was introduced, showed a significant increase in the amount of glycine compared to the KFCC11074 strain (i.e., 0.2 g/L vs. 3.2 g/L), although there was no significant difference in the amount of glutamic acid production between the two strains (64.2 g/L vs. 73 g/L).

From the foregoing, one of ordinary skill in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

ACCESSION NUMBER

Depositary Institution: Korean Culture Center of Microorganisms
Accession Number: KCCM12458P
Date of Deposit: Mar. 14, 2019
Depositary Institution: Korean Culture Center of Microorganisms
Accession Number: KCCM12459P
Date of Deposit: Mar. 14, 2019

The invention claimed is:

1. A method for producing glycine, comprising fermenting by culturing a microorganism of the genus Corynebacterium comprising ATP phosphoribosyltransferase (HisG) comprising an amino acid sequence of SEQ ID NO: 4, in which the 233$^{rd}$ amino acid of an amino acid sequence of SEQ ID NO: 4 is substituted with histidine (H), or the 233$^{rd}$ and 235$^{th}$ amino acids of an amino acid sequence of SEQ ID NO:4 are substituted with histidine (H) and glutamine (Q), respectively, in a medium.

2. The method according to claim 1, further producing glutamic acid.

3. The method according to claim 1, wherein the glycine is in the form of being comprised in a fermented composition.

4. The method according to claim 1, further comprising recovering glycine from the cultured medium.

5. The method according to claim 1, wherein the glycine productivity is increased compared to a microorganism of the genus *Corynebacterium* having ATP phosphoribosyltransferase without the substitution.

6. The method according to claim 1, wherein the ATP phosphoribosyltransferase consists of an amino acid sequence of SEQ ID NO: 5 or SEQ ID NO: 6.

7. The method according to claim 1, wherein the microorganism of the genus *Corynebacterium* is *Corynebacterium glutamicum*.

* * * * *

SEQUENCE LISTING

```
<160> NUMBER OF SEQ ID NOS: 18

<210> SEQ ID NO 1
<211> LENGTH: 65
<212> TYPE: DNA
<213> ORGANISM: Corynebacterium glutamicum

<400> SEQUENCE: 1
aattattcga ctaatatcct cccccaaaca cacattgata actgttgtgt ggaagaatgt    60
accga                                                               65

<210> SEQ ID NO 2
<211> LENGTH: 65
<212> TYPE: DNA
<213> ORGANISM: Artificial Sequence
<220> FEATURE:
<223> OTHER INFORMATION: hisEG promoter

<400> SEQUENCE: 2
aattattcga ctaatatcct cccccaaaca cacattgata actgttgtgt ggtataatgt    60
accga                                                               65

<210> SEQ ID NO 3
<211> LENGTH: 65
<212> TYPE: DNA
<213> ORGANISM: Artificial Sequence
<220> FEATURE:
<223> OTHER INFORMATION: hisEG promoter
```

<400> SEQUENCE: 3
aattattcga ctaatatcct cccccaaaca cacattgata actgttgtgt ggtataatgg    60
accga                                                                65

<210> SEQ ID NO 4
<211> LENGTH: 281
<212> TYPE: PRT
<213> ORGANISM: Corynebacterium glutamicum

<400> SEQUENCE: 4

Met Leu Lys Ile Ala Val Pro Asn Lys Gly Ser Leu Ser Glu Arg Ala
1               5                   10                  15

Met Glu Ile Leu Ala Glu Ala Gly Tyr Ala Gly Arg Gly Asp Ser Lys
            20                  25                  30

Ser Leu Asn Val Phe Asp Glu Ala Asn Val Glu Phe Phe Phe Leu
        35                  40                  45

Arg Pro Lys Asp Ile Ala Ile Tyr Val Ala Gly Gln Leu Asp Leu
    50                  55                  60

Gly Ile Thr Gly Arg Asp Leu Ala Arg Asp Ser Gln Ala Asp Val His
65                  70                  75                  80

Glu Val Leu Ser Leu Gly Phe Gly Ser Ser Thr Phe Arg Tyr Ala Ala
                85                  90                  95

Pro Ala Asp Glu Glu Trp Ser Ile Glu Lys Leu Asp Gly Lys Arg Ile
            100                 105                 110

Ala Thr Ser Tyr Pro Asn Leu Val Arg Asp Leu Ala Ala Arg Gly
        115                 120                 125

Leu Ser Ala Glu Val Leu Arg Leu Asp Gly Ala Val Glu Val Ser Ile
130                 135                 140

Lys Leu Gly Val Ala Asp Ala Ile Ala Asp Val Val Ser Thr Gly Arg
145                 150                 155                 160

Thr Leu Arg Gln Gln Gly Leu Ala Pro Phe Gly Glu Val Leu Cys Thr
                165                 170                 175

Ser Glu Ala Val Ile Val Gly Arg Lys Asp Glu Lys Val Thr Pro Glu
            180                 185                 190

Gln Gln Ile Leu Leu Arg Arg Ile Gln Gly Ile Leu His Ala Gln Asn
        195                 200                 205

Phe Leu Met Leu Asp Tyr Asn Val Asp Arg Asp Asn Leu Asp Ala Ala
    210                 215                 220

Thr Ala Val Thr Pro Gly Leu Ser Gly Pro Thr Val Ser Pro Leu Ala
225                 230                 235                 240

Arg Asp Asn Trp Val Ala Val Arg Ala Met Val Pro Arg Arg Ser Ala
                245                 250                 255

Asn Ala Ile Met Asp Lys Leu Ala Gly Leu Gly Ala Glu Ala Ile Leu
            260                 265                 270

Ala Ser Glu Ile Arg Ile Ala Arg Ile
        275                 280

<210> SEQ ID NO 5
<211> LENGTH: 281
<212> TYPE: PRT
<213> ORGANISM: Artificial Sequence
<220> FEATURE:
<223> OTHER INFORMATION: HisG(G233H)

<400> SEQUENCE: 5

```
Met Leu Lys Ile Ala Val Pro Asn Lys Gly Ser Leu Ser Glu Arg Ala
1               5                   10                  15

Met Glu Ile Leu Ala Glu Ala Gly Tyr Ala Gly Arg Gly Asp Ser Lys
            20                  25                  30

Ser Leu Asn Val Phe Asp Glu Ala Asn Asn Val Glu Phe Phe Leu
        35                  40                  45

Arg Pro Lys Asp Ile Ala Ile Tyr Val Ala Gly Gln Leu Asp Leu
    50                  55                  60

Gly Ile Thr Gly Arg Asp Leu Ala Arg Asp Ser Gln Ala Asp Val His
65                  70                  75                  80

Glu Val Leu Ser Leu Gly Phe Gly Ser Ser Thr Phe Arg Tyr Ala Ala
                85                  90                  95

Pro Ala Asp Glu Glu Trp Ser Ile Glu Lys Leu Asp Gly Lys Arg Ile
                100                 105                 110

Ala Thr Ser Tyr Pro Asn Leu Val Arg Asp Asp Leu Ala Ala Arg Gly
                115                 120                 125

Leu Ser Ala Glu Val Leu Arg Leu Asp Gly Ala Val Glu Val Ser Ile
    130                 135                 140

Lys Leu Gly Val Ala Asp Ala Ile Ala Asp Val Val Ser Thr Gly Arg
145                 150                 155                 160

Thr Leu Arg Gln Gln Gly Leu Ala Pro Phe Gly Glu Val Leu Cys Thr
                165                 170                 175

Ser Glu Ala Val Ile Val Gly Arg Lys Asp Glu Lys Val Thr Pro Glu
                180                 185                 190

Gln Gln Ile Leu Leu Arg Arg Ile Gln Gly Ile Leu His Ala Gln Asn
                195                 200                 205

Phe Leu Met Leu Asp Tyr Asn Val Asp Arg Asp Asn Leu Asp Ala Ala
    210                 215                 220

Thr Ala Val Thr Pro Gly Leu Ser His Pro Thr Val Ser Pro Leu Ala
225                 230                 235                 240

Arg Asp Asn Trp Val Ala Val Arg Ala Met Val Pro Arg Arg Ser Ala
                245                 250                 255

Asn Ala Ile Met Asp Lys Leu Ala Gly Leu Gly Ala Glu Ala Ile Leu
                260                 265                 270

Ala Ser Glu Ile Arg Ile Ala Arg Ile
            275                 280
```

<210> SEQ ID NO 6
<211> LENGTH: 281
<212> TYPE: PRT
<213> ORGANISM: Artificial Sequence
<220> FEATURE:
<223> OTHER INFORMATION: HisG(G233H/T235Q)

<400> SEQUENCE: 6

```
Met Leu Lys Ile Ala Val Pro Asn Lys Gly Ser Leu Ser Glu Arg Ala
1               5                   10                  15

Met Glu Ile Leu Ala Glu Ala Gly Tyr Ala Gly Arg Gly Asp Ser Lys
            20                  25                  30

Ser Leu Asn Val Phe Asp Glu Ala Asn Asn Val Glu Phe Phe Leu
        35                  40                  45

Arg Pro Lys Asp Ile Ala Ile Tyr Val Ala Gly Gln Leu Asp Leu
    50                  55                  60
```

```
Gly Ile Thr Gly Arg Asp Leu Ala Arg Asp Ser Gln Ala Asp Val His
 65                  70                  75                  80

Glu Val Leu Ser Leu Gly Phe Gly Ser Ser Thr Phe Arg Tyr Ala Ala
                 85                  90                  95

Pro Ala Asp Glu Glu Trp Ser Ile Glu Lys Leu Asp Gly Lys Arg Ile
            100                 105                 110

Ala Thr Ser Tyr Pro Asn Leu Val Arg Asp Leu Ala Ala Arg Gly
        115                 120                 125

Leu Ser Ala Glu Val Leu Arg Leu Asp Gly Ala Val Glu Val Ser Ile
    130                 135                 140

Lys Leu Gly Val Ala Asp Ala Ile Ala Asp Val Val Ser Thr Gly Arg
145                 150                 155                 160

Thr Leu Arg Gln Gln Gly Leu Ala Pro Phe Gly Glu Val Leu Cys Thr
                165                 170                 175

Ser Glu Ala Val Ile Val Gly Arg Lys Asp Glu Lys Val Thr Pro Glu
            180                 185                 190

Gln Gln Ile Leu Leu Arg Arg Ile Gln Gly Ile Leu His Ala Gln Asn
        195                 200                 205

Phe Leu Met Leu Asp Tyr Asn Val Asp Arg Asp Asn Leu Asp Ala Ala
    210                 215                 220

Thr Ala Val Thr Pro Gly Leu Ser His Pro Gln Val Ser Pro Leu Ala
225                 230                 235                 240

Arg Asp Asn Trp Val Ala Val Arg Ala Met Val Pro Arg Ser Ala
                245                 250                 255

Asn Ala Ile Met Asp Lys Leu Ala Gly Leu Gly Ala Glu Ala Ile Leu
            260                 265                 270

Ala Ser Glu Ile Arg Ile Ala Arg Ile
        275                 280

<210> SEQ ID NO 7
<211> LENGTH: 33
<212> TYPE: DNA
<213> ORGANISM: Artificial Sequence
<220> FEATURE:
<223> OTHER INFORMATION: Primer hisEG-pro-2mt-AF

<400> SEQUENCE: 7
gatcctctag agtcgacttc gacgaatccc tcg                                 33

<210> SEQ ID NO 8
<211> LENGTH: 32
<212> TYPE: DNA
<213> ORGANISM: Artificial Sequence
<220> FEATURE:
<223> OTHER INFORMATION: Primer hisEG-pro-2mt-AR

<400> SEQUENCE: 8
cggtacatta taccacacaa cagttatcaa tg                                  32

<210> SEQ ID NO 9
<211> LENGTH: 32
<212> TYPE: DNA
<213> ORGANISM: Artificial Sequence
<220> FEATURE:
<223> OTHER INFORMATION: Primer hisEG-pro-2mt-BF

<400> SEQUENCE: 9
gtggtataat gtaccgagtg aagacatttg ac                                  32
```

```
<210> SEQ ID NO 10
<211> LENGTH: 32
<212> TYPE: DNA
<213> ORGANISM: Artificial Sequence
<220> FEATURE:
<223> OTHER INFORMATION: Primer hisEG-pro-2mt-BR

<400> SEQUENCE: 10
atgcctgcag gtcgactgat acccaaatcg ag                              32

<210> SEQ ID NO 11
<211> LENGTH: 32
<212> TYPE: DNA
<213> ORGANISM: Artificial Sequence
<220> FEATURE:
<223> OTHER INFORMATION: Primer hisEG-pro-3mt-AR

<400> SEQUENCE: 11
cggtccatta taccacacaa cagttatcaa tg                              32

<210> SEQ ID NO 12
<211> LENGTH: 32
<212> TYPE: DNA
<213> ORGANISM: Artificial Sequence
<220> FEATURE:
<223> OTHER INFORMATION: Primer hisEG-pro-3mt-BF

<400> SEQUENCE: 12
gtggtataat ggaccgagtg aagacatttg ac                              32

<210> SEQ ID NO 13
<211> LENGTH: 34
<212> TYPE: DNA
<213> ORGANISM: Artificial Sequence
<220> FEATURE:
<223> OTHER INFORMATION: Primer hisG(G233H)-AF

<400> SEQUENCE: 13
gatcctctag agtcgacccc aaacaagggc tcgc                            34

<210> SEQ ID NO 14
<211> LENGTH: 28
<212> TYPE: DNA
<213> ORGANISM: Artificial Sequence
<220> FEATURE:
<223> OTHER INFORMATION: Primer hisG(G233H)-AR

<400> SEQUENCE: 14
cgtgccagtg gggataccgt tgggtggg                                   28

<210> SEQ ID NO 15
<211> LENGTH: 30
<212> TYPE: DNA
<213> ORGANISM: Artificial Sequence
<220> FEATURE:
<223> OTHER INFORMATION: Primer hisG(G233H)-BF

<400> SEQUENCE: 15
aaccccaggc ctatcccacc caacggtatc                                 30

<210> SEQ ID NO 16
<211> LENGTH: 33
<212> TYPE: DNA
<213> ORGANISM: Artificial Sequence
<220> FEATURE:
<223> OTHER INFORMATION: Primer hisG(G233H)-BR
```

```
<400> SEQUENCE: 16
atgcctgcag gtcgacgcaa ggttggcaac aac                          33

<210> SEQ ID NO 17
<211> LENGTH: 28
<212> TYPE: DNA
<213> ORGANISM: Artificial Sequence
<220> FEATURE:
<223> OTHER INFORMATION: Primer hisG(G233H/T235Q)-AR

<400> SEQUENCE: 17
cgtgccagtg gggatacctg tgggtggg                               28

<210> SEQ ID NO 18
<211> LENGTH: 30
<212> TYPE: DNA
<213> ORGANISM: Artificial Sequence
<220> FEATURE:
<223> OTHER INFORMATION: Primer hisG(G233H/T235Q)-BF

<400> SEQUENCE: 18
aaccccaggc ctatcccacc cacaggtatc                             30
```